United States Patent [19]

Chou

[11] Patent Number: 5,322,857

[45] Date of Patent: Jun. 21, 1994

[54] FOOD PRODUCTS HAVING INCREASED POTASSIUM CONTENT AND USE THEREOF IN ENHANCING GASTRIC ACID RESPONSE

[75] Inventor: Dorothy T. Chou, New York, N.Y.

[73] Assignee: Kraft General Foods, Inc., Northfield, Ill.

[21] Appl. No.: 54,815

[22] Filed: Apr. 28, 1993

[51] Int. Cl.$^5$ ........................ A61K 31/19; A23L 1/30
[52] U.S. Cl. ........................ 514/574; 426/2; 426/74
[58] Field of Search ............... 424/600, 656, 670, 679, 424/722; 514/574

[56] References Cited

U.S. PATENT DOCUMENTS 4,166,860 9/1979 Douglas et al. .................... 514/400

FOREIGN PATENT DOCUMENTS

0534024A2 3/1993 European Pat. Off. .

OTHER PUBLICATIONS

Berglindh, T.: The Effects Of $K^+$ and $Na^+$ On Acid Formation In Isolated Gastric Glands. Acta Physiol Scand Spec Suppl: 55–58, 1977.

Davis, T. L., et al.: Acid Secretion, Potential, And Resistance Of Frog Stomach In $K^+$-free Solutions. Am J Physiol 209: 146–152, 1965.

Ray, T. K. & Tague, L. L.: Secretagogue-induced Transport Of $H^+$ and $K^+$ By In Vitro Amphibian Gastric Mucosa. Biochemical Pharmacol 29: 2755–2758, 1980.

*Primary Examiner*—Frederick E. Waddell
*Assistant Examiner*—Raymond J. Henley, III
*Attorney, Agent, or Firm*—Thomas A. Marcoux; Thomas R. Savoie

[57] ABSTRACT

Coffee products and other comestibles having an increased content of potassium are useful to enhance the gastric acid response of persons having abnormally low gastric acid secretion such as persons having gastric atrophy or atrophic gastritis. Preferred coffee beverages have an added potassium content of at least 1% by weight based on the dry weight of coffee solids in the beverage.

7 Claims, 1 Drawing Sheet

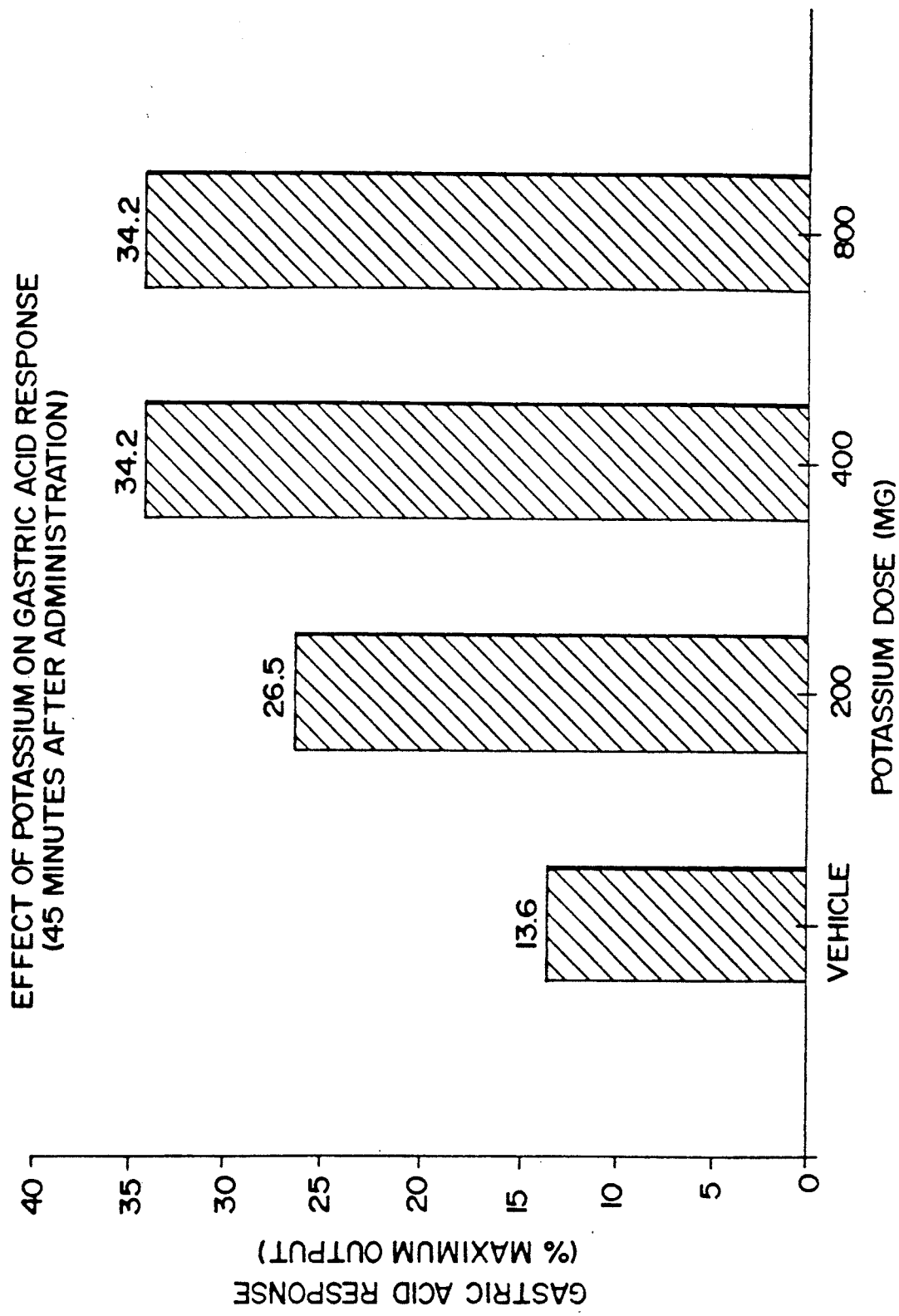

FOOD PRODUCTS HAVING INCREASED POTASSIUM CONTENT AND USE THEREOF IN ENHANCING GASTRIC ACID RESPONSE

FIELD OF THE INVENTION

This invention relates to coffee products having an increased content of potassium and to the use of foods and beverages having an increased potassium content to enhance the gastric acid response in persons with low gastric acid secretion, especially individuals having atrophic gastritis or gastric atrophy.

BACKGROUND OF THE INVENTION

It has been known that potassium ion plays an important role in gastric H+ transport and it has been demonstrated that K+ is necessary for the maintenance of acid secretion. Moreover, K+ is a normal essential component of gastric juice.

The prevalence of atrophic gastritis and gastric atrophy among our population is well recognized. These conditions result in gastric acid hyposecretion or hypochlorhydria. The physiological consequences of hypochlorhydria include a decreased secretion of intrinsic factor for vitamin $B_{12}$ absorption, bacterial overgrowth in the proximal small intestine, and altered proximal small intestinal pH. Under normal conditions, most bacteria swallowed or ingested with food are destroyed by gastric acid. The bacteria that overgrow in the upper small bowel in atrophic gastritis individuals may affect the absorption of certain nutrients by binding or metabolizing these nutrients and/or reducing their bioavailability.

In addition, a high intraluminal pH of the stomach and proximal small intestine may prevent the release of specific nutrients from food complexes (e.g. fiber, phytate, protein) as a result of a lack of pH-dependent dissociation and/or acid pepsin digestion. In general, trace minerals such as iron, zinc and copper precipitate with phytate at pH values greater than 4. Mineral-fiber interactions are also pH dependent and the extent of binding of mineral by dietary fiber increases with increasing pH. For example, zinc associated with a protein-phytate complex shows low bioavailability which could be related to the decreased digestibility of protein when complexed to phytate. A rise in stomach pH values, together with decreased pepsin activity, may encourage the formation of protein-mineral-phytate complexes or prevent the dissociation of such complexes. Thus, the absorption or digestion of select nutrients are dependent upon adequate gastric acidity.

It is an object of the invention to provide a method of enhancing gastric acid response in persons with low gastric acid secretion, especially individuals having atrophic gastritis or gastric atrophy. It is a further object to provide a method of oral administration of potassium to enhance the gastric acid response in such persons. It is a further object to provide coffee products having an enhanced potassium content.

BRIEF SUMMARY OF THE INVENTION

The foregoing and other objects which will be apparent to those of ordinary skill in the art are achieved in accordance with the invention by providing a method of enhancing gastric acid response in a person with lower than normal gastric acid secretion, especially individuals having atrophic gastritis or gastric atrophy which comprises orally administering to said person, within sixty minutes of the consumption of food by that person, a comestible containing an added edible potassium compound, the amount of the comestible administered being sufficient to provide an effective amount of added potassium, and by providing a coffee product selected from the group consisting of roasted coffee beans, roasted and ground coffee, soluble coffee, a liquid coffee concentrate, and a coffee beverage, said coffee product having in intimate admixture therewith an added edible, water soluble potassium compound in an amount such that the total potassium content of the coffee product is sufficient to provide a total potassium content of at least 200 mg per eight ounce serving of a coffee beverage prepared from said coffee product.

BRIEF DESCRIPTION OF THE DRAWING

The drawing shows the effect of potassium on gastric acid response 45 minutes after administration.

DETAILED DESCRIPTION OF PREFERRED EMBODIMENTS

The drawing is a graphical illustration of gastric acid response as a function of potassium dose.

Coffee products in accordance with the invention include roasted coffee beans, roasted and ground coffee, soluble (or "instant") coffee, liquid coffee concentrates or coffee beverages.

In accordance with the invention, an added edible and water soluble potassium compound, preferably a salt, is provided in intimate admixture with a comestible, preferably a coffee product, in an amount such that the total potassium content (as potassium) in a normal serving of the comestible, such as a six or eight ounce serving of a coffee beverage prepared from the coffee product, is at least 200 mg. Potassium can be tolerated in much higher amounts, but has a noticeable taste and is therefore preferably added in an amount such that the total amount of potassium is not more than 2000 mg, more preferably 200 to 1100 mg, per such normal serving. The taste attributable to potassium may be mitigated by the use of compounds such as potassium gluconate, potassium citrate, and the like or mixtures thereof and/or by the use of known "masking agents", which mask the bitter taste of potassium.

The amount of added potassium needed to bring the total potassium content to at least 200 mg per serving will of course depend on the natural potassium content of the coffee beverage. The potassium content of coffee varies somewhat but is typically about 1.8%, dry weight basis, for roast and ground coffee and about 3.5%, dry weight basis, for soluble coffee. The strength of the coffee beverages also varies. Typically the solids content of coffee beverages in the U.S.A. for soluble coffee is about 0.5 to 1.2% and for roast and ground coffee is from about 0.4 to 0.7% whereas in some European countries the solids content can be twice as much. In a typical example of roast and ground coffee beverage, with a brewer yield of 25%, and a coffee solids content of 0.6%, and assuming extraction of all of the potassium content of the coffee, the potassium content of an eight ounce serving (236 g) of the beverage is 102 mg (236 g×0.006×0.018/0.25). Similarly, the potassium content of an eight ounce serving of a soluble coffee beverage with a 1% coffee solids content would be 83 mg (236 g×0.01×0.035). The amount of potassium needed to be added to these coffee products brings the total potassium content of this serving of these coffee beverages to at least 200 mg would be about 100 mg per serving in the case of the roast and ground coffee beverage or about 1.8% [100÷(236×0.006×4×10³)×100] of the roast and ground coffee, dry weight basis, and about 117 mg per serving in the case of the soluble coffee beverage, or about 5% [117÷(236×0.01×10³)×100] of the soluble coffee, dry weight basis. In general, therefore, the potassium content of the coffee product (as potassium) added in accordance with the invention is such that the potassium content of an eight ounce serving of a 1% coffee solids-containing coffee beverage prepared from the coffee product and attributable to the added potassium compound is at least about 100 mg, preferably from about 100 to about 1900 mg. Again, the added potassium content of the beverage is preferably kept low to minimize off-taste. Accordingly, the content of added potassum in the coffee product is preferably such that the content of added potassium in an eight ounce serving of a 1% coffee solids-containing coffee beverage prepared from the coffee product is preferably about 100–1000 mg and more preferably about 100–700 mg.

In terms of the coffee products used to make the coffee beverages, the amount of potassium (as potassium) added to a roast and ground product will generally be about 0.2 to 20% by weight, preferably about 0.3 to 10%, and more preferably about 0.5 to 5%, based on the weight of the roast and ground coffee, and the amount added to a soluble coffee will generally be about 1 to 30% by weight, preferably about 1 to 20% and more preferably about 3 to 10% by weight, dry basis, based on the weight of the soluble coffee.

In a coffee beverage, the amount of added potassium, as potassium, is at least 1% and generally about 1 to 30% by weight based on the weight of the coffee solids, preferably 1 to 20%, and more preferably 2 to 10%, same basis.

Suitable edible and water soluble potassium compounds include potassium chloride, potassium citrate, potassium gluconate, potassium carbonate, potassium bicarbonate, potassium sorbate, etc.

By "water soluble" is meant that the compound is soluble to the extent of at least 10 grams per liter of water at 20° C.

The potassium compound can be provided in intimate admixture with the coffee product or other comestible in any of several convenient ways. In the case of coffee beans, the potassium compound is preferably deposited thereon by spraying a solution of the potassium compound on the beans or infused into the beans. In the case of liquid coffee products, the potassium compound is preferably dissolved in the product. For instant coffee, the potassium compound is preferably provided in a coffee extract before conventional drying, such as spray drying or freeze drying, utilized to make a particulate instant coffee product, but can be coated onto, or simply physically mixed with, the particulate product after its production. Thus it will be understood that the expression "in intimate admixture therewith" is not limited to physical mixtures of particles, but includes coatings and, in the case of liquid coffee products, solutions.

As is shown in Example 1 which follows, it has been found that the oral administration of an effective amount of potassium enhances gastric acid response. The invention thus has utility in enhancing gastric acid response in persons with an abnormally low gastric acid response such as individuals having atrophic gastritis or gastric atrophy. In addition, the coffee products of the invention have utility in normal healthy persons, in enhancing the absorption or digestion of certain minerals and nutrients due to enhanced gastric acidity. In general, the amount of added potassium administered, as potassium, should be at least 100 mg, preferably from 100–1900 mg and more preferably 100–1000 mg. The potassium is administered to aid the absorption or digestion of food and is thus administered within about 60 minutes of food consumption, preferably from about 30 minutes before eating to about 30 minutes after eating.

In accordance with the invention, the added potassium is administered in a comestible, preferably a beverage and more preferably a coffee beverage as described herein. Where a coffee beverage is used, the beverage preferably has an added potassium content of at least about 4%, preferably 4–50%, and more preferably 4–30% by weight based on the dry weight of the coffee solids in the beverage.

EXAMPLE 1

A randomized, double-blind, 4-way crossover study in 8 healthy male volunteers was conducted. Maximum gastric acid output was determined before administration of potassium citrate. After administration of potassium citrate, gastric acid secretion was evaluated by measuring the pH, volume and concentration of $H^+$ in gastric aspirates every 15 minutes. Gastric pH was monitored constantly with a Digitrapper.

All subjects underwent a pentagastrin stimulated gastric secretion test. Subjects checked into the test center the evening before the day of the test. Before testing, all subjects fasted at least 12 hours. On the morning of pentagastrin screening, the entire contents of the stomach were aspirated, followed by administration and immediate aspiration of 15 mL of ambient temperature water. Subjects were then allowed to equilibrate for 30 minutes before beginning the first portion of the pentagastrin screening. After equilibration, the contents of the stomach were aspirated in two consecutive 15 minute intervals. Pentagastrin (6 $\mu$g/kg) was then administered subcutaneously. Following pentagastrin administration, stomach secretions were collected quarter-hourly for 1.5 hours. All aspirates were analyzed for pH, acid concentration, and volume. Acid concentrations were multiplied by the corresponding volume to yield titratable acidity, measured in mEq. To determine the baseline Maximum Acid Output (MAO), the mean of the four highest mEq readings over the six post-pentagastrin collection intervals was calculated. Similarly, the baseline Peak Acid Output (PAO) was determined by averaging the two highest consecutive mEq readings.

On four separate occasions, each separated by at least one week, subjects checked into the test center the evening before execution of study procedures and fasted for a minimum of twelve hours. The entire contents of the stomach were aspirated, followed by administration and immediate aspiration of 15 mL of ambient temperature water. Subjects were then allowed to equilibrate for 30 minutes. At ten minute intervals after the 30-minute equilibration period, three 150 mL aliquots of ambient water were administered and immediately removed.

Potassium citrate (200, 400 or 800 mg potassium; equivalent to 554.6, 1109.2 or 2218.4 mg of the monohydrous salt) were weighed and dissolved in 150 mL of 37° C. water on the dosing mornings.

After the three 150 mL water administrations, subjects were dosed twice at 15-minute intervals with 0 (Dose A), 200 (Dose B), 400 (Dose C), or 800 (Dose D) mg of potassium dissolved in 150 mL of water. The contents of the stomach were aspirated every fifteen minutes for 2 hours after administration of the first dose. All aspirates were analyzed for pH, acid concentration and volume. Acid concentrations were multiplied by the corresponding volume to yield titratable acidity, measured in mEq. All mEq values were also expressed as a percentage of both the MAO and PAO, as determined after pentagastrin stimulated secretion testing. Results are presented in Tables I and II.

TABLE I

Titratable Acidity (mEq) Expressed as a Percentage of Baseline Maximum Acid Output (% MAO)

| Mean | Time (h) (Hours after initial administration) | | | | | |
|---|---|---|---|---|---|---|
| | 0.25 | 0.50 | 0.75 | 1.00 | 1.50 | 2.00 |
| Dose A (Water) | 23.27 | 22.36 | 13.61 | 13.11 | 22.24 | 21.89 |
| Dose B (200 mg) | 34.65 | 36.08 | 26.54 | 20.09 | 14.94 | 20.20 |
| Dose C (400 mg) | 32.74 | 33.34 | 34.22 | 22.97 | 14.97 | 21.36 |
| Dose D (800 mg) | 44.95 | 40.18 | 34.23 | 36.26 | 26.38 | 19.05 |

TABLE II

Titratable Acidity (mEq) Expressed as a Percentage of Baseline Peak Acid Output (% PAO)

| Mean | Time (Hours after initial administration) | | | | | |
|---|---|---|---|---|---|---|
| | 0.25 | 0.50 | 0.75 | 1.00 | 1.50 | 2.00 |
| Dose A (Water) | 18.05 | 17.30 | 10.35 | 10.64 | 17.16 | 16.22 |
| Dose B (200 mg) | 27.01 | 27.79 | 20.92 | 16.13 | 11.78 | 15.64 |
| Dose C (400 mg) | 25.41 | 26.29 | 26.15 | 18.17 | 11.63 | 16.88 |
| Dose D (800 mg) | 34.78 | 29.49 | 24.83 | 27.24 | 19.89 | 15.23 |

The MAO results of the pentagastrin screening ranged from a low of 3.3041 mEq (Subject No. 2) to a high of 9.7641 (Subject No. 5). Similarly, the PAO ranged from 4.3379 (Subject No. 7) to 10.7177 (Subject No. 5).

Mean titratable acidity (acid concentration × volume, expressed in mEq) values are presented in Table III.

TABLE III

Titratable Acidity (mEq) in Each Sampling Time Interval

| Mean | Time (Hours after initial administration) | | | | | |
|---|---|---|---|---|---|---|
| | 0.25 | 0.50 | 0.75 | 1.00 | 1.50 | 2.00 |
| Dose A (Water) | 1.3654 | 1.3929 | 0.7578 | 0.8691 | 1.3669 | 1.1969 |
| Dose B (200 mg) | 1.9172 | 1.8706 | 1.5442 | 1.1265 | 0.9009 | 1.2329 |
| Dose C (400 mg) | 1.6931 | 1.7182 | 1.7936 | 1.3438 | 0.8590 | 1.3470 |
| Dose D (800 mg) | 2.3696 | 2.2025 | 1.9066 | 1.8666 | 1.5215 | 1.1796 |

Statistically significant differences (p values less than 0.05) were detected between the water (Dose A) and 800 mg dose level at 0.25, 0.75 and 1 hours, and between the water (Dose A) and 400 mg dose level at 0.75 hour. In all cases, Doses C (400 mg) and D (800 mg) produced the higher titratable acidity. Many other comparisons approached significance, but, due to the small sample size significance was not achieved.

Individual titratable acid values were divided by the patient's maximum acid output (MAO) to yield MAO% values. These are summarized in Table I. Statistically significant differences ($p<0.05$) were detected between the water (Dose A) and 800 mg dose level at 0.25, 0.75 and 1 hours, and between the water (Dose A) and 400 mg dose level at 0.75 hour.

Individual titratable acid values were divided by the patient's peak acid output (PAO) to yield PAO% values. These are summarized in Table II. Statistically significant differences ($p<0.05$) were detected between the water (Dose A) and 800 mg dose level at 0.25, 0.75 and 1 hours, and between the water (Dose A) and 400 mg dose level at 0.75 hour.

The effect on gastric acid secretion 45 minutes after its administration in the study is shown in the drawing which shows in graphic form the mean values of gastric acid response, as a percent of maximum acid output, as a function of the potassium dose, 45 minutes after the initial administration of potassium. The drawing thus shows in graphical form the data from the third column (0.75 hour) of Table I. As mentioned above, the gastric acid response values for a potassium dose of 400 and 800 mg relative to the administration of water are statistically significant. The fact that statistical significance was achieved with only 8 subjects indicates that the differences are real indeed. In one individual, an 800 mg dose produced acid level 88.8% as high as his maximum acid output (MAO). For other individuals, this percentage was often in the 50% range.

EXAMPLE 2

A double-blind, randomized, nutritionally-controlled, 2-way crossover study was carried out in eight healthy elderly hyposecretors (mean age is 67.6 years, basal acid output less than $5\pm2$ mmol/h, and/or maximal acid output less than $15\pm2$ mmol/h). The purpose of this study was to evaluate the effects of potassium in food system on micronutrient bioavailability. Sugar Free Tang fortified with 800 mg potassium (2218.4 mg potassium citrate monohydrate) was used in this study. Either 6 oz regular Sugar Free Tang or potassium-enriched Sugar Free Tang was given 15 minutes prior to a meal of Post Bran Flakes cereal (high fiber and micronutrients fortified) and skim milk, twice a day at breakfast and at afternoon snack. Subjects followed these two different diets for 10 days each, with a washout of at least 7 days between two phases. Blood samples were collected for micronutrients analysis at baseline and last three days of diet treatments. Five micronutrients were measured; iron (Fe), zinc (Zn), and magnesium (Mg) by atomic absorption spectrophotometry, and vitamin $B_{12}$ and folate by radioimmunoassay (RIA). Analyses of variance were performed on Fe, Zn, Mg, $B_{12}$, and folate AUC parameters, with baseline concentration used as covariates. The results show that administration of potassium-enriched beverage significantly increases the plasma levels of Fe (667.2 vs. 348.7 mcg.h/dL, $p<0.005$) and vitamin $B_{12}$ (1233 vs 899 pmol.h/L, $p<0.01$) in comparison to control beverage. No significant diet effect was found for Zn, Mg, and folate. The significant increases in plasma levels of Fe and vitamin $B_{12}$ by potassium together with our previous finding that potassium increases gastric acid output, indicate that potassium may increase micronutrient bioavailability via directly stimulating gastric acid secretion in elderly hyposecretors. Potassium can thus be used in foods, especially in beverages and coffee, to improve micronutrient status among elderly hyposecretors.

EXAMPLE 3

Potassium is added to a conventional commercial spray dried soluble coffee product (typically approximately 3.5% potassium db) by dissolving in the coffee extract before spray drying 64 parts by weight potassium citrate (8 parts by weight of potassium) per 100 parts by weight of coffee solids in the extract. The resultant spray dried product contains approximately 7.2% potassium, dry basis. An eight ounce serving of a coffee beverage having a 1% coffee solids content contains approximately 195 mg of added potassium and a total potassium content of approximately 278 mg. The coffee beverage is useful for oral administration of potassium to enhance gastric acid response in accordance with the invention.

EXAMPLE 4

8.8 parts by weight of powdered food grade potassium citrate (1.1 parts by weight of potassium) is physically mixed with 100 parts by weight of a commercial, conventionally processed roast and ground coffee (containing approximately 1.8% potassium). A coffee beverage is then prepared from the modified coffee using a conventional automatic coffee maker. The beverage contains approximately 1% coffee solids and the roast yield is approximately 25%. The potassium provided by both the coffee solids and the added potassium citrate is fully extracted into the brew. An eight ounce serving of the beverage contains approximately 105 mg of added potassium and the total potassium content of the beverage is approximately 275 mg. The coffee beverage is useful for the oral administration of potassium to enhance gastric acid response in accordance with the invention.

What is claimed is:

1. A method of enhancing gastric acid response in a person with a below normal gastric acid secretion which comprises orally administering to said person, within 60 minutes of the consumption of food by that person, a comestible containing an added edible potassium compound, the amount of comestible administered being sufficient to provide an effective amount of added potassium.

2. A method according to claim 1 wherein the comestible comprises a coffee beverage and wherein the amount of beverage administered is sufficient to provide a total of at least 100 mg of added potassium.

3. A method according to claim 1 wherein the comestible comprises a coffee beverage and wherein the amount of beverage administered is sufficient to provide a total of from 100 to 1900 mg of added potassium.

4. A method according to claim 2 wherein the amount of added potassium compound is sufficient to provide at leas 1% by weight of added potassium based on the weight of coffee solids in the beverage.

5. A method according to claim 2 wherein the amount of added potassium compound is sufficient to provide from 1 to 30% by weight of added potassium based on the weight of coffee solids in the beverage.

6. A method according to claim 2 wherein the amount of added potassium compound is sufficient to provide from 1 to 20% by weight of added potassium based on the weight of coffee solids in the beverage.

7. A method according to claim 1 wherein the person has atrophic gastritic or gastric atrophy.

* * * * *